United States Patent
Riebel et al.

(10) Patent No.: US 6,587,200 B1
(45) Date of Patent: Jul. 1, 2003

(54) METHOD OF MEASURING PARTICLE SIZES

(76) Inventors: Ulrich Riebel, Dorfstrasse 35, 03096, Briesen (DE); Udo Kraeuter, Voelklinger Strasse 24, 51375, Leverkusen (DE)

(*) Notice: Subject to any disclaimer, the term of this patent is extended or adjusted under 35 U.S.C. 154(b) by 0 days.

(21) Appl. No.: 09/381,367
(22) PCT Filed: Mar. 12, 1998
(86) PCT No.: PCT/EP98/01490
§ 371 (c)(1), (2), (4) Date: Feb. 14, 2001
(87) PCT Pub. No.: WO98/41840
PCT Pub. Date: Sep. 24, 1998

(30) Foreign Application Priority Data

Mar. 19, 1997 (DE) .......................... 197 11 494

(51) Int. Cl.⁷ .............................................. G01N 15/02
(52) U.S. Cl. ....................................... 356/336; 356/335
(58) Field of Search .................................. 356/335, 336

(56) References Cited

U.S. PATENT DOCUMENTS

| 3,733,548 | A | * | 5/1973 | Coulter et al. ............. 324/71.1 |
| 3,779,070 | A | * | 12/1973 | Cushman et al. ............. 73/628 |
| 3,975,084 | A | | 8/1976 | Block |
| 4,110,044 | A | | 8/1978 | Pettersson et al. |
| 4,318,180 | A | | 3/1982 | Lundqvist et al. |
| 4,529,309 | A | | 7/1985 | Pettersson et al. |
| 4,539,649 | A | | 9/1985 | Michaelis et al. |
| 4,752,131 | A | | 6/1988 | Eisenlauer et al. |
| 4,988,190 | A | * | 1/1991 | Miles .......................... 356/28 |
| 5,015,094 | A | | 5/1991 | Oka et al. |
| 5,095,451 | A | * | 3/1992 | Allen .......................... 702/29 |
| 5,121,629 | A | * | 6/1992 | Alba .......................... 73/602 |

FOREIGN PATENT DOCUMENTS

| DE | 3138159 | 4/1983 |
| DE | 3344122 | 6/1985 |
| EP | 0427093 | 5/1991 |

* cited by examiner

Primary Examiner—Michael P. Stafira
Assistant Examiner—Roy M. Punnoose
(74) Attorney, Agent, or Firm—Dilworth & Barrese LLP (57) ABSTRACT

The invention relates to a process for measuring particle size by measuring the attenuation of radiation after its passage through a defined measuring section containing a disperse system. According to the invention the temporally fluctuating transmission signal is recorded with variable time or spatial resolution. The transmission signals recorded then undergo a non-linear operation. The result of that non-linear operation is represented and analyzed as a spectral curve, i.e., as a function of the spatial or temporal resolution.

20 Claims, 6 Drawing Sheets

METHOD OF MEASURING PARTICLE SIZES

BACKGROUND OF THE INVENTION

The invention relates to a process for measuring particle size by measuring the attenuation of radiation after its passage through a defined measuring section containing a disperse system.

Many fields of process engineering require an exact characterization of disperse systems. In disperse systems there is a disperse phase, i.e. solid, liquid or gaseous particles in a continuous phase, that is, a liquid or gaseous phase. Characterization is generally based on particle size distribution and particle volume concentration. Ideally these quantities are measured in situ so as to avoid errors due to sampling, dilution and the like. There is also a need for simple and cost-effective process control methods.

There are known particle size measurement processes which use statistical data taken from transmission measurements. For this purpose a measurement of mean transmission (dependent solely on the particle projection area concentration, or on volume concentration and mean particle size) is expressed in relation to the standard deviation of transmission measured with a fixed beam diameter. The standard deviation is dependent on the volume concentration—although there is no single-valued function for this (Gregory (in the Journal of Colloid and Interface Science, Vol. 105, No. 2, 1985, p. 357) FIG. 11, $\Phi=C_V$)— and on the mean particle size. By this means it is possible to determine the concentration and mean particle size for a specific range of values, but it is not possible to measure a particle size distribution in this way.

SUMMARY OF THE INVENTION

The objective of the invention is to provide an improved process for measuring particle size which eliminates the need to perform a calibration procedure using the material being measured.

According to the invention this objective is achieved on the basis of a generic process by the temporally fluctuating transmission signal is recorded with variable temporal or spatial resolution. The transmission signals undergo a non-linear operation and the result of that non-linear operation is represented and interpreted as a spectral curve, i.e. as a function of the spatial or temporal resolution.

According to the invention this takes advantage of the fact that the temporal fluctuations of the transmission signal, together with the electrical noise, are an expression of the probability of the presence of various particle size classes in the volume being measured. According to the invention described herein, the information on particle size distribution and particle volume concentration contained in the fluctuation of the transmission signal is used systematically for particle size measurement. An essential step in the process according to the invention is that the transmission signals undergo a non-linear operation. The non-linear operation can, for example, be a squaring operation, logarithmisation, or indeed an analytical function, for example, a function of the form $(T)^N$ or $\exp\{T\}$, where T is transmission and N any real number. However, in general terms it is also possible to use other non-linear operations in the process according to the invention.

It is advantageous if the signal is recorded with high temporal and spatial resolution and represented and analyzed as an auto power density spectrum in the form of a special non-linear operation.

Signal recording and processing with variable temporal resolution can be achieved by a variety of low-pass, high-pass and/or band-pass combinations, and the result of the non-linear operation can be represented and analyzed of the low pass, high-pass or band pass.

The signals can be recorded digitally, and a sliding average with variable averaging parameter can be formed as digital low pass, high pass and/or band pass.

According to an especially advantageous embodiment, the cross-section of the measurement beam can be variable in size and/or shape, so as to produce an optic low pass, high pass and/or band pass.

It is especially advantageous if the process consists of the combination of the following process steps:
  creation of the signals in a small optic measurement cross-section,
  variable electrical or digital averaging,
  subjecting the average values formed to a non-linear operation,
  repeating the previous process steps with at least one larger measurement cross-section, and
  comparison of the results from the non-linear operations, and the determination on that basis of the particle size distribution, particle concentration and particle velocity.

Alternatively, an advantageous embodiment of the process consists of the combination of the following process steps:
  creation of signals and variation of optic measurement cross-sections,
  subjecting these signals to a non-linear operation,
  creation of signals using a very small optic measurement cross-section,
  known fixed or variable electronic and digital averaging of the signals produced,
  subjecting these signals to the same non-linear operation as they have already undergone,
  comparison of the results from the non-linear operations and determination of the particle size distribution, particle concentration and particle velocity on the basis of that comparison.

According to an alternative embodiment of the process according to the invention, the primary beam can be divided into several sub-beams and passed through the measurement section in the form of those sub-beams. These sub-beams can be used to form variable optic low passes or band passes, by additive or subtractive superposition of the transactions measured with the sub-beams.

The creation of such sub-beams makes it possible to carry out the non-linear operation by means of a non-linear combination—a multiplication, for example—of the transmissions of two or more sub-beams. According to various embodiments of the invention the sub-beams can run through the suspension in different directions. First, they can run parallel to a plane set transverse to the direction of flow. Alternatively, they can run parallel to a plane which is set parallel to the direction of flow of the suspension. Finally, the sub-beams can intersect at a single point, i.e. the measurement volume. Alternatively they may cross in various different planes lying one above the other, viewed in the direction of flow of the suspension.

The process according to the invention is now described on the basis of a preferred embodiment example illustrated in the accompanying drawings, in which.

DESCRIPTION OF THE PREFERRED EMBODIMENTS

By way of example, the measurement and interpretation operation is described here for a process in which the signal is recorded optically with various different low-pass characteristics, by varying the diameter of the measurement beam.

Hence the instantaneous transmission $T_D$<t> is continually measured with e.g. 10 different beam diameters D, after which the non-linear operation (NLO, in this example a squaring operation) is carried out separately for each measurement value; following that NLO, the average value of the signal, $E_D$ <$T^2$>, is formed separately for each of the 10 beam diameters. At the same time the average of the successive measurement values is formed for each of the 10 beam diameters, resulting in the same value E<T> (within the limits of unavoidable error) for all beam diameters.

Figure 1:
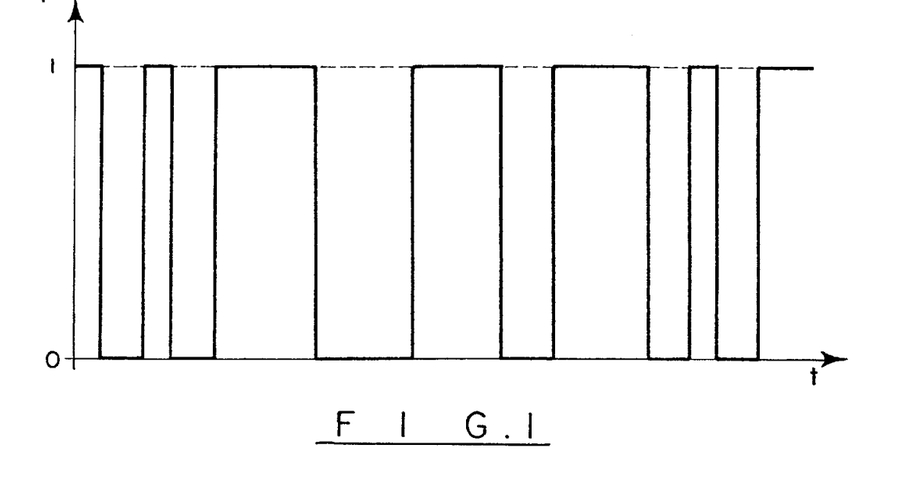
FIG. 1 is a graph of measurement of a signal over time.

If one considers the curve over time of the signal $T_D$ <t> for any very small beam diameter D (D <<x) and a radiation-impermeable particle of diameter x, $T_D$ jumps only between the values 0 (beam blocked by a particle) and 1 (full transmission of beam through a gap between the particles), see FIG. 1. In this situation, subject to fulfilment of the condition D <<x, D can be decreased within a wide range (i.e. by several decades) without causing any significant change in the curve of $T_D$<t>.

On the other hand, if one considers $T_D$ <t> in the range D >> x, the signal over time is almost constant, with only slight fluctuations. Here again, no significant changes result from any further increase in D.

Since the measurement for a very large beam diameter D (D >> particle size x) corresponds to the formation of an average from a large number of successive measurements:

$$E^2<T>=E_{D\to\infty}<T> \quad (1)$$

or, in general terms $$NLO<E<T>>=E_{D\to\infty}<NLO<T>> \quad (1a)$$

Since volume and time averaging are generally equivalent, equation 1(a) applies for any NLO.

If we measure the curve ED <NLO<T>> with a suspension of particles of equal size, in each of the ranges D<<x and D>>x we find constant gradients in each case, with an S-shaped transition between them in the range D≈x.

The exact shape and height of the S-shaped step depend on the NLO selected.

The specific NLO of "squaring" (like some other possible NLOS) has the characteristic that the transmission values T=0 and T=1 are not changed by the operation, so that:

$$E_{D\to 0}<T^2>=E_{D\to 0}<T>=E<T> \quad (2)$$

Figure 2:
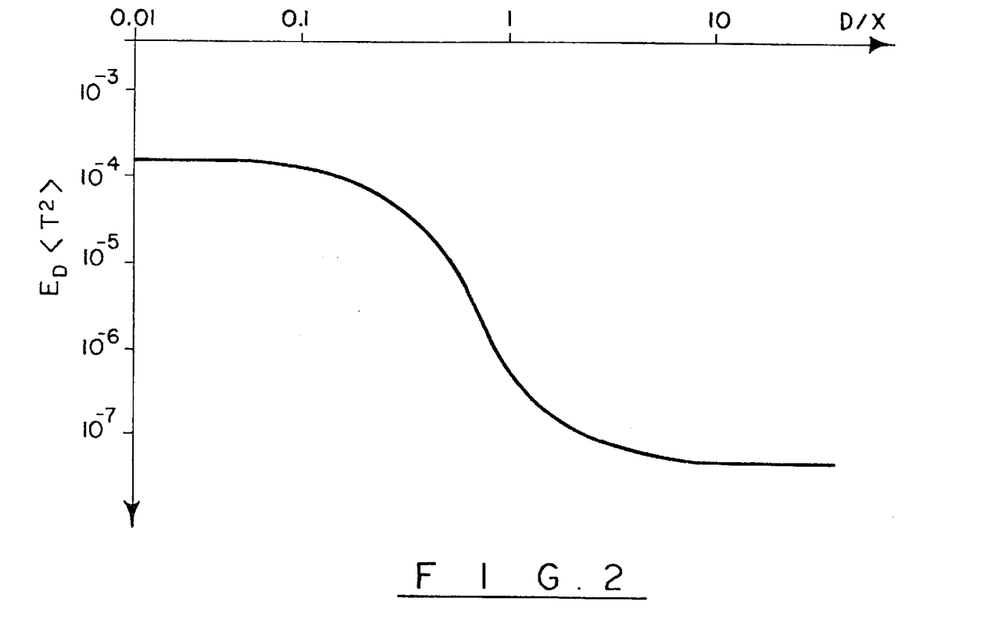
FIG. 2 is a graph of a curve of average value of the signal for mono-disperse glass beads over the beam diameter.

FIG. 2 shows a curve for $E_D$<$T^2$> for monodisperse glass beads, plotted over beam diameter D/x standardized with the particle size.

When shown in appropriately standardised form (see FIG. 3), the curve for the value $E_D$<$T^2$> can be represented in a uniform manner for any particle sizes x and for any particle concentrations and course lengths.

Figure 3:
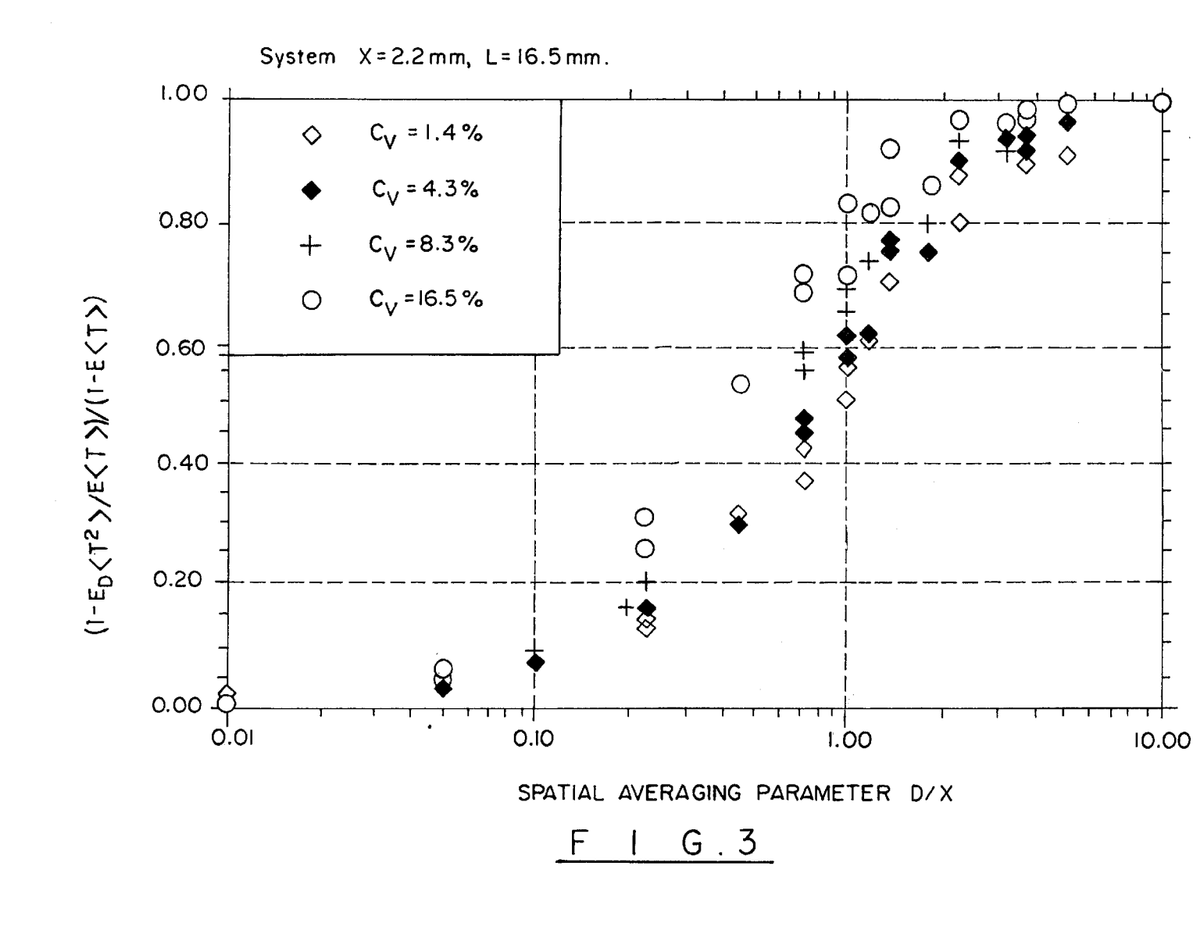
FIG. 3 is a graph of the average value of the signal of FIG. 2 in standardized form.

For a monodisperse material, the particle size can be read directly from a diagram according to FIG. 2 or 3, from the position of the half-value of the step height on the D/x axis. The following applies:

$$(D/X)_{half\,value} \approx 0.80 \quad (3)$$

Figure 4:
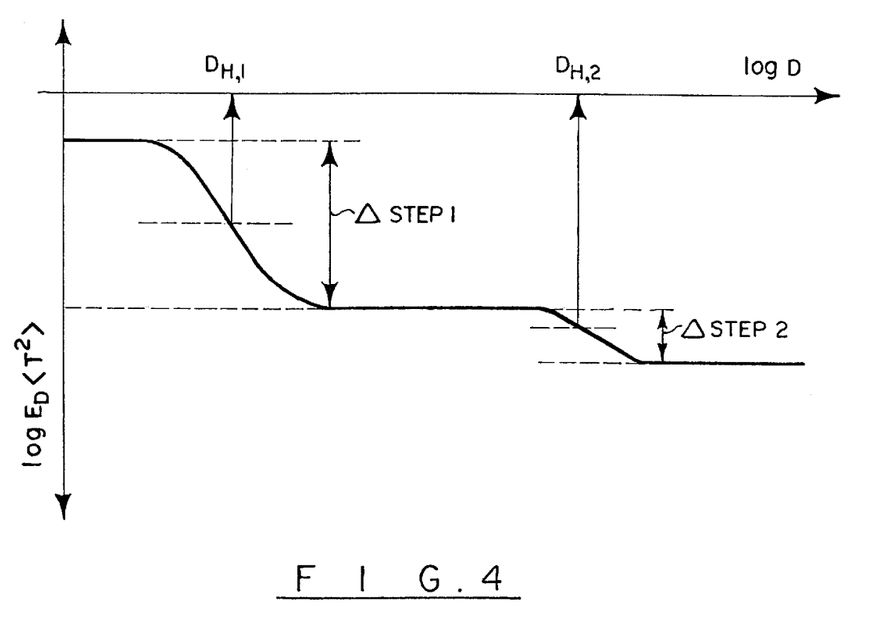
FIG. 4 is a graph of the average value of the signal over particular diameter for a mix of two mono-disperse fractions.

By insertion of the value for $D_{half-value}$, which is known from the measurement, it becomes possible to solve equation 3 for the required particle size. It is also possible to directly calculate the particle concentration, e.g. expressed by the projection surface concentration $C_{pf}$ (particle projection area/suspension volume), according to Bouger-Lambert-Beer's equation and with equation (1):

$$-\tfrac{1}{2}\ln\sqrt{E_{D\to\infty}<T^2>}=-\ln E<T>=K_{ext}\cdot C_{Pf}\cdot \Delta I \quad (4)$$

where $\Delta I$ is the course length of the beam through the suspension, $C_{Pf}$ is the projection area concentration, and $K_{ext}$ is the extinction coefficient; for the case of radiation-impermeable particles as shown here $K_{ext}=1$ The requirement will generally be to interpret not a measurement made on a monodisperse material, but a measurement made on a particle size distribution. The principle of this kind of interpretation will now be described, initially using the example of a measurement made on a material produced by the mixture of two monodisperse fractions. If the particle diameters of the two fractions are sufficiently far apart, $E_D$<$T^2$> over D can be plotted as a 2-step curve, see FIG. 4. $D_{half-value}$ can be read off separately for each of these two steps, and can be interpreted as per equation 3.

Similarly, the two step heights can be interpreted separately as per an extended version of equation 4:

$$-\Delta_{step\,i}(\ln E<T^2>=K_{ext,i}\cdot \Delta I \quad (5)$$

where $\Delta_{step\,i}$ is the height of the i-th step $K_{ext,i}$ is the extinction coefficient of fraction i and $C_{Pf,i}$ is the proj. area concentration of the i-th fraction For the case where the values of the diameters of the different particle fractions are very close together or where a wide particle size distribution is involved, direct interpretation of the type described above is no longer possible.

A form of interpretation which is of general applicability is seen in the situation where the measured curve of E<$T^2$> is represented by the superposition of the signals produced by N individual particle fractions.

Where squaring is used as the NLO, a linear superposition applies according to the following:

$$\ln(E\langle T_{D}^2\rangle) = \sum_{j=1}^{N}\ln(E_j\langle T_{D}^2\rangle) \quad (6)$$

with the individual summands in $E_j$<$T_D^2$> being given by $$\ln E_j<T_D^2>=-K_{ext,j}\cdot C_{Pf,j}\cdot \Delta I\cdot S<x_j, D> \quad (7)$$

In this context S <$x_j$, D>, as "statistical coefficient", is a function of the ratio D/$x_j$, and is read from the standardized representation as per FIG. 3 as $$S<x_j, D>\equiv S<D/x_j>=1+(1-E_D<T^2>/E<T>)/(1-E<T>) \quad (8)$$

This means that using equations (6) to (8), $\ln(E\langle T_D \rangle)$ can be represented as the linear function $$\ln E\langle T_{D2}\rangle = C_{Pf}\Delta l \cdot \sum_{j=1}^{N} K_{ext,j} \cdot S\langle x_j, D\rangle \cdot q_2\langle x_j\rangle \Delta x_j \quad (9)$$

where $C_{Pf}$ is the overall projection area concentration of the particles, $q_2 \langle x_j \rangle$ the projection area distribution density, and $\Delta x_j$ the breadth of the respective particle size interval j.

If we now measure $mi = \ln E\langle T_D^2 \rangle$ for $i=1 \ldots M$ for different diameters $D_i$ of the measurement beam, a linear system of equations can be obtained from equation (9):

$$\vec{m} = \Delta l \, \vec{\vec{S}} \cdot \vec{g} \quad (10)$$

where $\vec{m}$ is the vector of measured ml $\vec{g}$ is the vector of the required quantities $g_j = C_{Pf} \cdot K_{ext,j} \cdot q_2 \langle x_j \rangle \Delta x_j$, where $K_{ext,j}$ is known.

and $\vec{\vec{S}}$ is the matrix of statistical coefficients Sij

This system of equations can be solved using normal methods for the required quantities of particle size distribution and particle concentration.

It is also possible to use some simplified solution procedures, which are accordingly faster or less sensitive to measurement errors.

The width of the S-shaped curve, which can for example be represented as the quotient $D_{90}D_{10}$ (position of 90% value or 10% value of the step height) provides, by comparison with the width for a monodisperse fraction, a measurement for the width of the particle size distribution.

Alternatively, interpretation can be carried out by storing a number of curves which have been measured or calculated for known particle distributions in a data file. It is then possible to select from the data file the curve which is closest to the curve being measured, and in this way, provided there is a sufficient body of data in the file, the particle size distribution can be calculated. It is also possible to train a neuronal network with signals of known particle distributions, and then use this for the interpretation of measured curves.

These methods can also be used to solve non-linear systems of equations produced when the contributions of individual particle size fractions are superposed in a non-linear manner. This is to be expected in the case of high particle concentrations, for example, or with the use of certain NLOs.

An equivalent to measurement using a number of different beam diameters is obtained by measuring the transmission with a single measurement beam which is as thin as possible, and conveying this signal to e.g. 10 different electrical low passes with different time constants which process the signal simultaneously. The 10 low passes then provide 10 different output signals which are subjected, in parallel, to the same NLO (in our example a squaring operation), followed by an averaging process in which they give different average values $E_\tau \langle T^2 \rangle$. Simultaneously with the above, the average value of the original transmission signal is again formed and also squared, producing the value $E^2\langle t \rangle$.

By plotting these values over the time constant of the low pass one also obtains an S-shaped curve which corresponds exactly to the curve for a measurement with various different measurement beam diameters and plotting over D, since the volume low pass (characterised by the measurement beam diameter D) and the time low pass (characterised by the time constant) are similar in every way. The only difference lies in the fact that in the case of the volume low pass direct allocation between the beam diameter $D_{half-value}$ and the average particle diameter x is possible (equation), whereas this is not possible for the time low pass. Instead, in the case of the time low pass it is rather the velocity at which the particle moves through the measurement volume which plays a role; in this context the following relation applies:

$$x = 0.8 \cdot \tau_{half-value} \cdot V. \quad (12)$$

However, the particle velocity v is often not known. The invention therefore provides for a possibility of measurement with variable temporal $\tau$ (which is generally much easier than using measurement beams with various different diameters), and simultaneously measuring D' with a single, precisely known volume low pass. Given the complete similarity between the two curves it is now possible, using the identity $$E_\tau \langle T^2 \rangle = E_D \langle T^2 \rangle \text{ for } D = \tau \cdot v \quad (13)$$

which holds for the entire curve, to produce the relationship between the time and volume scales. For interpretation purposes, this means that it is possible to determine not only the particle size and concentration, but also the velocity of the particles.

Alternatively, the velocity v can also be determined using any independent measurement process. If a measurement process is carried out using several (at least 2) sub-beams, an especially advantageous embodiment consists in the determination of the velocity of the particles by methods known in the art from the cross-correlation between the transmissions for the two sub-beams.

Figure 5:
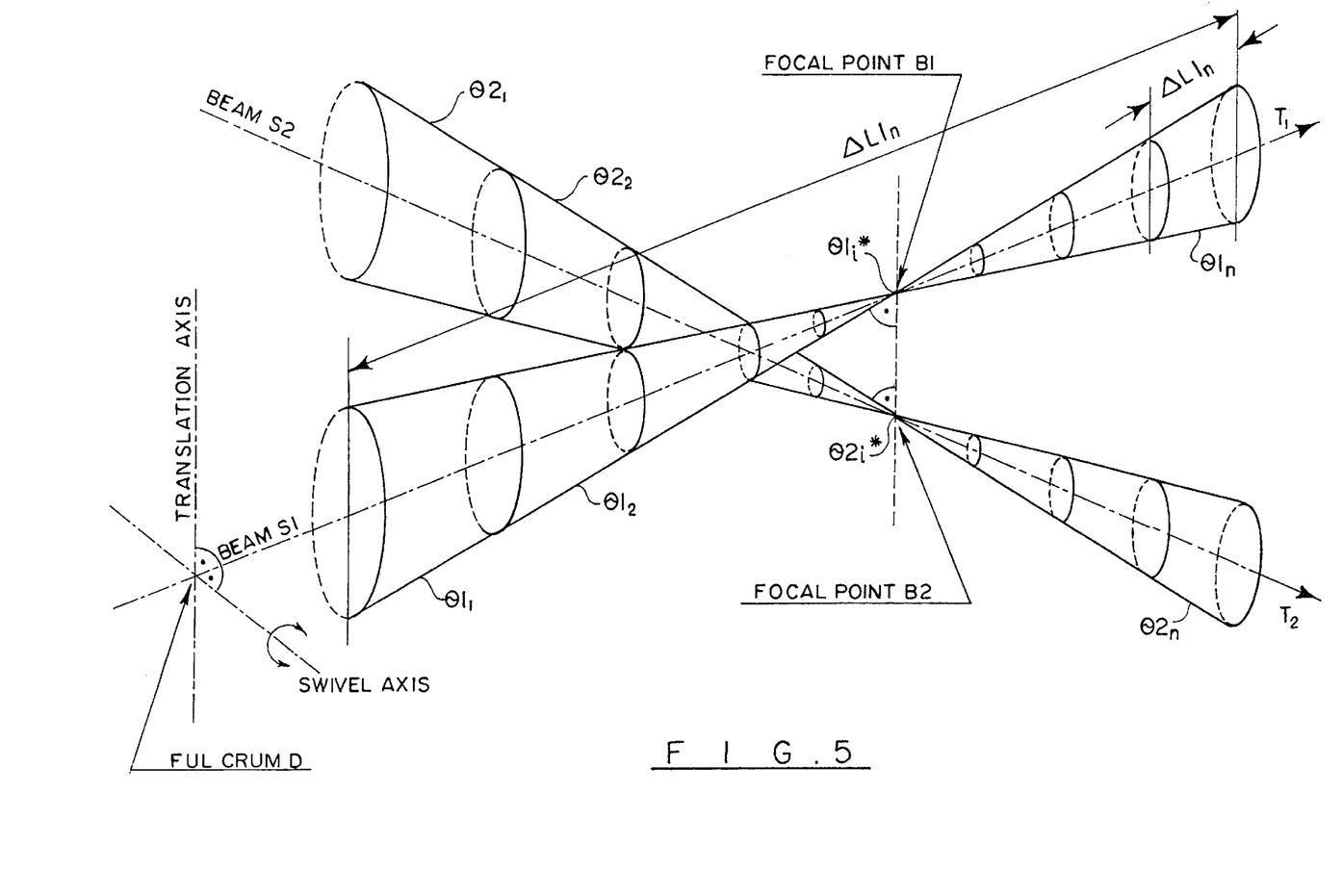
FIG. 5 schematically illustrates intersection of two measurement beams.

A preferred embodiment of the invention is arrived at as follows:

Two measurement beams are directed in such a way that they cross within the measurement section, with the smallest distance between the measurement beams being designated as $\delta$, see FIG. 5.

The two transmissions $T_1$, $T_2$ of the two beams are recorded separately, with high temporal and spatial resolution. A high spatial resolution is achieved in particular by focusing beams 1 and 2 on the cross-over point at focal points $B_1$ and $B_2$ respectively. The distance $\delta$ can be varied, for example by the displacement of beam 1 in the plane set by $B_1$, $B_2$ and D, by a swivelling or parallel movement.

According to the preferred embodiment, $\delta$ can be reduced to zero, such that the focal points $B_1$, $B_2$ coincide.

The transmissions $T_1$, $T_2$ can then be obtained as products from transmission values $\theta_{1j}$, $\theta_{2j}$, which can be allocated to single small sections of the relevant beam course $\Delta|_{1i}$, $\Delta|_{2i}$:

$$T_1 = \prod_i \theta_{1i} \text{ using } \Delta l_1 = \sum_i \Delta l_{1i} \quad (14)$$

and $$T_2 = \prod_i \theta_{2i} \text{ using } \Delta l_2 = \sum_i \Delta l_{2i} \quad (15)$$

Generally, values $\theta_{1i}$ do not correlate in any way with values $\theta_{2i}$, but are rather fluctuations which are statistically independent of each other. This applies for all $\theta_{1i}$, $\theta_{2i}$ if the distance $\delta$ is greater than the largest particle present, and if the particles move perpendicular to the length $\delta$ set by B1, B2. In this case, if we form the product $\theta_{1i} \cdot \theta_{2i}$ from the two transmissions, the expected value of the product $\theta_{1i} \cdot \theta_{2i}$ will be equal to the product of the expected values:

$$E\langle \theta_{1i} \cdot \theta_{21} \rangle = E\langle \theta_{1i} \rangle \cdot E\langle \theta_{2i} \rangle \quad (16)$$

Hence it makes no difference whether the temporal average (=expected value) is formed before or after the multiplication operation.

However, if δ is smaller than $X_{max}$ or if δ→0, the transmissions $\theta_{1i}$ and $\theta_{2i}$ from the immediate environment of B1, B2 are correlated with each other, or identical (for δ=0). Hence specifically for the limit case δ=0 the following applies:

$$E<\theta_1{}^*_i \cdot \theta_2 \delta_i> = E<\theta^{*2}> \tag{17}$$

$$\text{since } \theta_1 \delta_i = \theta_2{}^*_i = \theta^* \tag{18}$$

and correspondingly $$E<\theta_1{}^*_i \cdot \theta_2{}^*_i> \neq E<\theta_1{}^*_i> \cdot E<\theta_2{}^*_i> \tag{19}$$

According to the preferred embodiment, at this point the NLO (non-linear operation) is carried out by multiplying the two measured transmissions T2, T2, so that $$T1 \cdot T2 = \prod_i \theta_{1i} \cdot \prod_i \theta_{2i} \tag{20}$$
$$= \prod_i (\theta_{1i} \cdot \theta_{2i})$$

If δ is now selected as >x, $\theta_{1i}$, $\theta_{2i}$ are not correlated at any point, and the following applies, in accordance with equation (16):

$$\log(E\langle T1 \cdot T2\rangle) = \log(E\langle T2\rangle \cdot E\langle T2\rangle) \tag{21}$$
$$= \log\left(\prod_i (E\langle\theta_{1i}\rangle \cdot E\langle\theta_{2i}\rangle)\right)$$

If, on the other hand, δ is selected as <<x or δ/x→0, the identity between $\theta_2{}^*_i$ has to be taken into account, and the following applies:

$$\lim_{\delta/x\to 0} \log(E\langle T1\ T2\rangle) = \log\left(\prod_i (E\langle\theta_{1i}\rangle \cdot E\langle\theta_{2i}\rangle)\right) \log\frac{E\langle\theta_i^{*2}\rangle}{E\langle\theta_{1i}^*\rangle \cdot E\langle\theta_{2i}^*\rangle} \tag{22}$$

The 2nd expression in equation (22) shows how log (E <T1 T2>) changes in the area around δ/x=1.

Since it has also been arranged that beams 1 and 2 are to pass through the focal points B1, B2 at the cross-over point, at that location the spatial resolution will be higher than the particle diameter x, and the sub-transmissions $\theta_1{}^*$, $\theta_2{}^*$ will jump in each case between the values 0 and 1. Hence it again applies that $$E<\theta_i^{*2}> = E<\theta_i^*> = E<\theta_{1i}^*> = E<\theta_{2i}^*> \tag{23}$$

or $$\lim_{\delta/x\to 0} \log(E\langle T1\ T2\rangle) = \log\left(\prod_i (E\langle\theta_{1i}\rangle \cdot E\langle\theta_{2i}\rangle)\right) \log\frac{1}{E\langle\theta_i^*\rangle} = \tag{24}$$
$$\lim_{\delta/x \gg 1} \log(E\langle T1\ T2\rangle) - \log(E\langle\theta_i^*\rangle)$$

Figure 6:
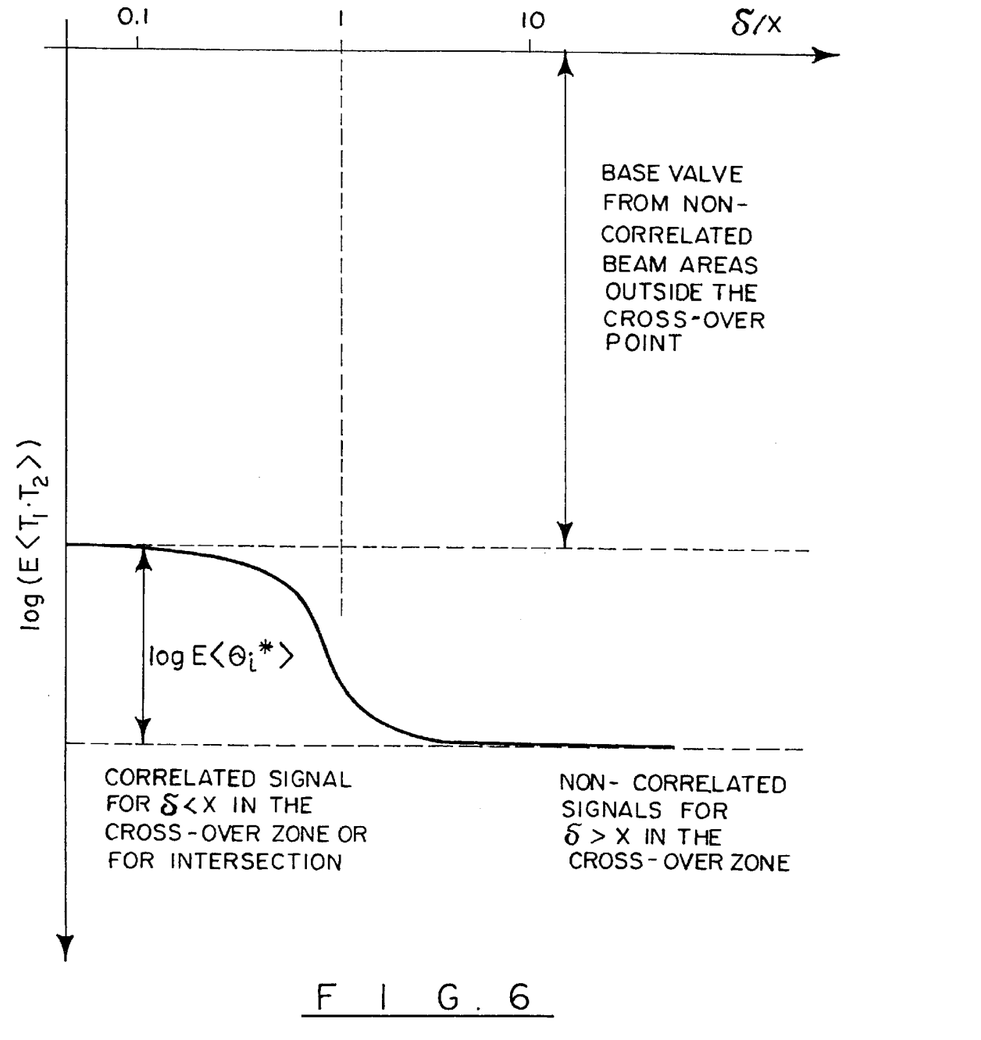
FIG. 6 is a graph of the log of the average signal value of the mono-disperse phase suspension of FIG. 5 against distance between the two beams of FIG. 5.

If we now plot log ($E<T1 \cdot T_2>$) as the spectrum of δ/x for the case of a monodisperse suspension, we obtain the curve shown in FIG. 6. The result is again a step-shaped curve, where from the position of the step at δ/x≈1 it is again possible to determine the particle size, and from the height of the step it is possible to determine the quantity of particles which have flowed through the intersection zone and created the correlated signal. Hence the interpretation is similar in every way to that applicable in the embodiment working with a variation of the beam diameter or the time constant of averaging. The special advantage of this embodiment is that in this way it is possible to measure the particle concentration and particle size distribution with a high level of local resolution.

According to a variant of this embodiment, the section δ set by the points B1, B2 is directed parallel to the direction of movement of the particles. If δ is now selected as >x, then signal components $\theta_1{}^*$, $\theta_2{}^*$ are identical, with a displacement in time, e.g. in the case of transport in the direction of B1 to $B_2$:

$$\theta_1^*<t> = \theta_2^*<t+\delta/v> \tag{25}$$

v is the velocity of the particles. As before, the signal components arising remote from the cross-over point are not correlated with each other.

If we now form the product $$T_1<t> \cdot T_2<t+\tau> \tag{26}$$

with displacement in time τ

$$\rho = \delta/v \tag{27}$$

then this corresponds to the calculation of the product for the case δ=0, i.e. the beams intersect at the cross-over point.

Figure 7:
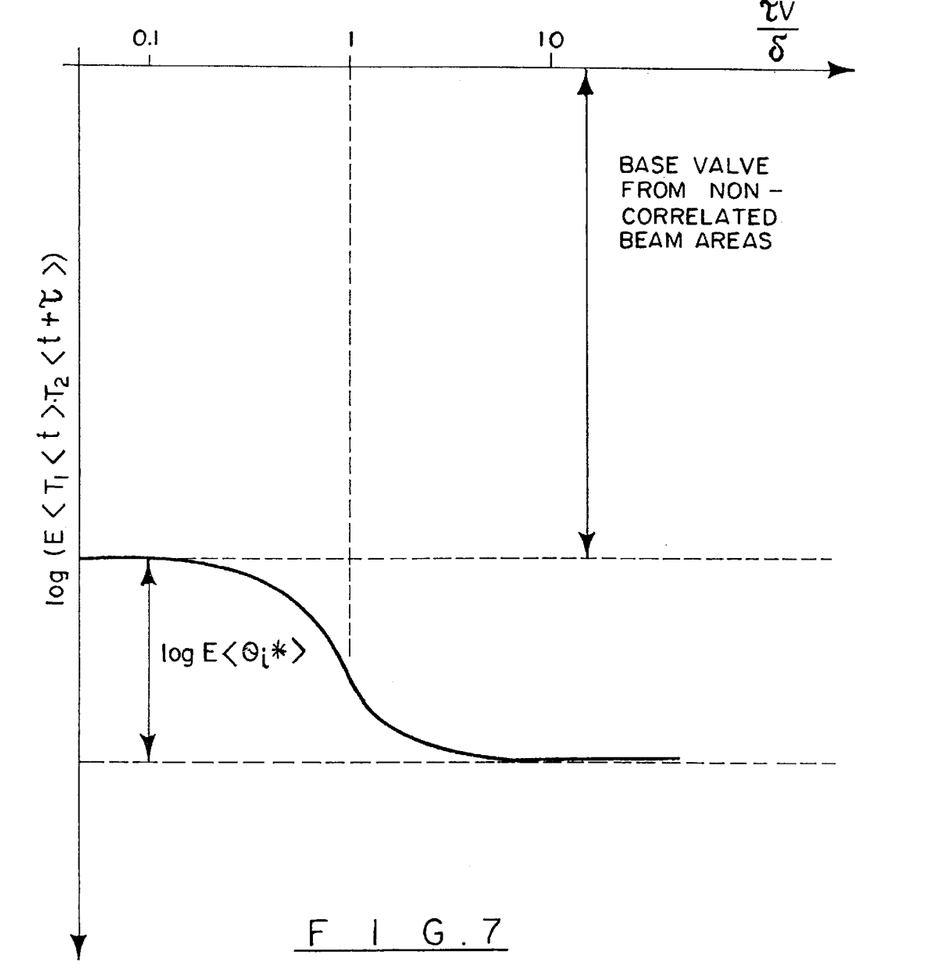
FIG. 7 is a graph of the log of the cross-correlation product of the two beams of FIG. 5 for any fixed distance therebetween as a function of standardized placement in time.

We now measure, for any fixed δ, the transmissions T1 and T2 with a high level of temporal resolution, form the cross-correlation product $T_1<t> \cdot T_2<t+\tau>$) with variable displacement in time τ and plot log ($E<T_1<t> \cdot T_2<t+\tau>$) as a function of the standardized displacement in time $$\frac{(\tau \cdot v)}{\delta},$$

(cf FIG. 7).

The variation of τ at $\vec{v}\,//B_1B_2$ is therefore, in terms of the result, analogous to a variation of δ at $\vec{v}\perp B_1B_2$. The amount for velocity v required for interpretation purposes can be determined by independent measurement procedures. Particularly for fixed δ where δ≈0, v can be determined as v=δ/$\tau_{max}$, where $\tau_{max}$ refers to the displacement in time τ for which the cross-correlation $$T1<t> \cdot T_2<t+\tau>$$

has its maximum.

What is claimed is:

1. Process for measuring particle size by measuring the attenuation of radiation after its passage through a defined measurement section in which there is a disperse system, comprising the steps of
    recording the temporally fluctuating transmission signals with variable temporal or spatial resolution,
    subjecting all these transmission signals to a non-linear operation, and
    representing and interpreting the result of that non-linear operation as a spectral curve, i.e., as a function of the spatial or temporal resolution.

2. Process according to claim 1, wherein the non-linear operation is a squaring operation.

3. Process according to claim 1, wherein the non-linear operation is a logarithmization operation.

4. Process according to claim 1, wherein the non-linear operation is an analytical function, for example of the following form:

(T)$^N$ or exp{T}, where T is the transmission and N any real number other than 0 or 1.

5. Process according to claim 1, wherein the signal is recorded with a high temporal and spatial resolution and represented and interpreted as an auto-power density spectrum.

6. Process according to claim 1 in which the signal is recorded with variable temporal resolution by various low pass, high pass and/or band pass combinations, and where the result of the non-linear operation is represented and interpreted as a function of the time constant of the low pass, high pass and/or band pass.

7. Process according to claim 6, wherein the signals are recorded digitally and undergo a sliding average formation with variable averaging parameter as digital low pass, high pass and/or band pass.

8. Process according to claim 6, wherein the cross-section of a measurement beam is variable in its size and/or shape in order to create an optic low pass, high pass and/or band pass.

9. Process according to claim 1, wherein it has the following process steps:

generating the signals in a small optic measurement cross-section beam diameter (D≦particle size x), conducting variable electronic or digital averaging, subjecting the average values formed to a non-linear operation, repeating the three previous process steps with at least one larger measurement cross-section, and comparing the results from the non-linear operations, and then determining, by said comparing, the particle size distribution, particle concentration and particle velocity.

10. Process according to claim 1, wherein the process has the following process steps:

generating signals and varying the optic measurement cross-section, subjecting these signals to the non-linear operation, generating signals with a very small optic measurement cross-section (beam diameter D<particle size x), conducting known fixed or variable electronic and digital averaging of the signals produced, subjecting the signals to the same non-linear operation as already undergone, and comparing the results from the non-linear operations and determining the particle size distribution, particle concentration and particle velocity on the basis of that comparison.

11. Process according to claim 1, wherein several sub-beams are passed through the measurement section.

12. Process according to claim 11, wherein variable optic low passes or band passes are created by additive or subtractive superposition of the transmissions measured with the sub-beams.

13. Process according to claim 11 wherein the non-linear operation is carried out by means of a non-linear combination, especially a multiplication, of the transmissions of two or more sub-beams.

14. Process according to claim 11 wherein the sub-beams are directed in such a way as to run through the disperse system parallel to a plane set transverse to the direction of flow of the flowing particles of the disperse system.

15. Process according to claim 11, wherein the sub-beams are directed in such a way as to run through the disperse system parallel to a plane which is set parallel to the direction of flow of the flowing particles of the disperse system.

16. Process according to claim 11 to 15, wherein the sub-beams are directed in such a way as to intersect at one point (measurement volume), or to cross in various different planes lying one above the other in the direction of flow of the flowing particles of the disperse system.

17. Process according to claim 11 or 15[sic], wherein the sub-beams are directed in such a way as to cross within the measurement volume, with the smallest interval distance between sub-beams (δ) being variable, and allowed to be 0 in a limit case.

18. Process according to claim 17, wherein one sub-beam is kept fixed, while the other sub-beam can be adjusted in order to vary the smallest interval distance (δ).

19. The process of claim 1, comprising the explicit steps of (d) maintaining intensity and frequency of the irradiation constant, (e) measuring the transmittal signal (intensity or amplitude) with high resolution in space and time, thereby resolving changes of transmission occurring when particles pass through the beam of irradiation, (f) varying the resolution in time by either (1) applying a gliding average or frequency filter on said fluctuating transmission signal, whereby the relevant frequencies are related to time of passage of a particle through the beam, or (2) varying beam diameter or distance between two beams in a cross-over point, whereby intensity of both said beams are then added to form an average, (d) subjecting said still-fluctuating signal (whereby fluctuation is dampened depending upon degree of averaging), to a nonlinear operation by either (1) Conducting a root, square, or logarithmic analysis to obtain a transformed signal that is still fluctuating, or (2) Multiplying said fluctuating transmission signals measured with said two beams, and (e) determining expectation, i.e., long-term average of said thus transformed signal, relating to times which are much larger than time a particle requires to travel across a beam diameter or distance between said two beams.

20. The process according to claim 1, wherein irradiating frequency remains unchanged, with only transmitted radiation being measured.

* * * * *